Figure 1:
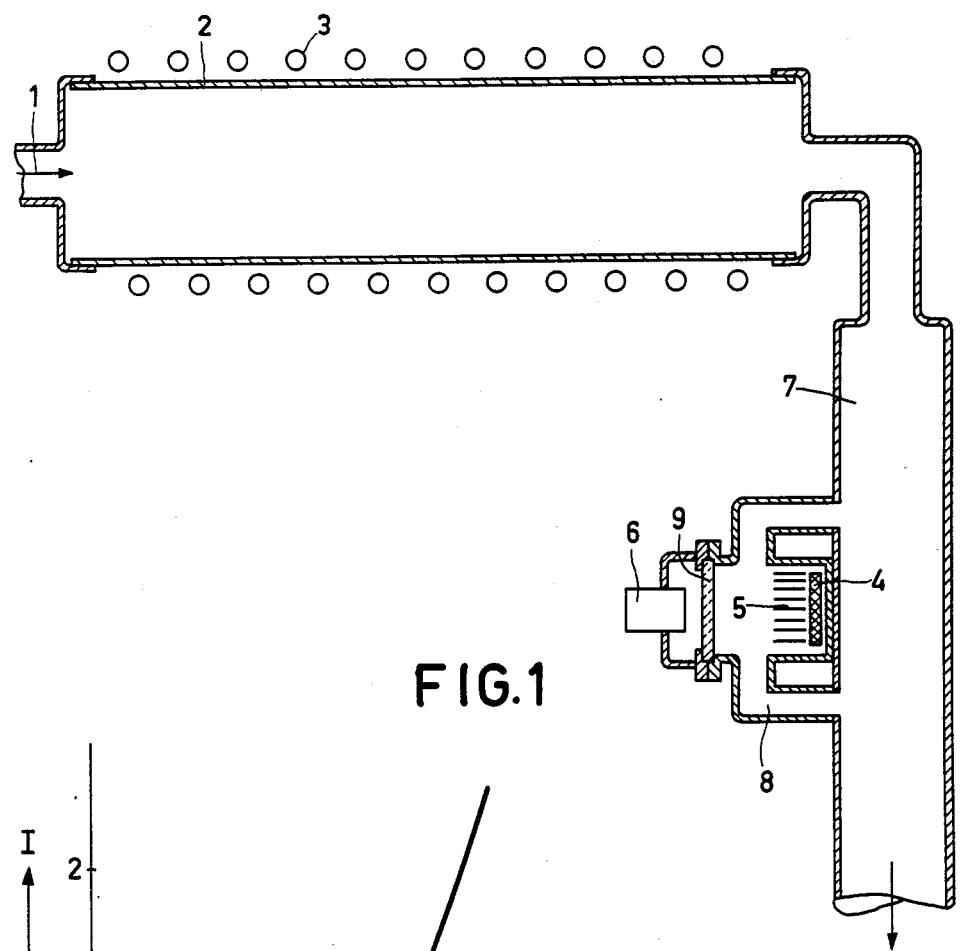

United States Patent [19]

Beenakker et al.

[11] Patent Number: 4,666,857
[45] Date of Patent: May 19, 1987

[54] METHOD OF DETERMINING FLUORINE

[75] Inventors: Cornelis I. M. Beenakker; Raoul P. J. Van De Poll, both of Eindhoven, Netherlands

[73] Assignee: U.S. Philips Corporation, New York, N.Y.

[21] Appl. No.: 457,323

[22] Filed: Jan. 12, 1983

Related U.S. Application Data

[63] Continuation of Ser. No. 209,773, Nov. 24, 1980, abandoned.

[30] Foreign Application Priority Data

Nov. 26, 1979 [NL] Netherlands .......................... 7908560

[51] Int. Cl.$^4$ ............................................ G01N 21/76
[52] U.S. Cl. ...................................... 436/124; 436/172
[58] Field of Search ................... 436/124, 172; 422/52

[56] References Cited

PUBLICATIONS

Mogab et al., "Plasma Etching of Si and SiO$_2$-the Effect of Oxygen Additions to CF$_4$ Plasmas", *J. Appl. Phys.*, 49(7), Jul. 1978.

*Primary Examiner*—Peter Chin
*Attorney, Agent, or Firm*—Paul R. Miller

[57] ABSTRACT

A method of determining the concentration of fluorine in a gas flow is provided, in which the gas flow is passed through a gas discharge space in which fluorine atoms are formed and after leaving the space the formed fluorine atoms in the gas flow are reacted with a substance to emit luminescent radiation and the intensity of the radiation is measured. Elemental silicon is chosen as a material for the substance and is provided so as to be optically separated from the space.

2 Claims, 2 Drawing Figures

METHOD OF DETERMINING FLUORINE

This is a continuation of application Ser. No. 209,773, filed Nov. 24, 1980, abandoned.

The invention relates to a method of determining the concentration of fluorine in a gas flow, in which the gas flow is passed through a gas discharge space in which fluorine atoms are formed and, after leaving the space, the formed fluorine atoms in the gas flow are reacted with a substance to emit luminescent radiation and the intensity of the radiation is measured.

A method of the above-mentioned kind is known from the Journal of Applied Physics, Vol 49, pp. 3796–3803 (1978). After leaving a gas discharge space, gaseous chlorine ($Cl_2$) is injected in the gas flow.

Fluorochlorine (FCl) and chlorine atoms are formed from the chlorine and the fluorine atoms. The measured luminescence is that of the recombination of chlorine atoms.

This prior method is a titration method, the luminescence intensity increases until all atomic fluorine has been converted, which can only be established by measuring the luminescence intensity as a function of the injected quantity of chlorine.

An important disadvantage of this prior method is that in the form described it is discontinuous and hence unfit for determining the concentration of fluorine in continuous gas flows with varying fluorine content.

If the method is to be used in a continuous form, a quantity of chlorine which is larger than corresponds to the concentration of fluorine atoms maximally to be determined must also be injected continuously.

The disadvantage hereof is that large quantities of chlorine are objectionable from a point of view of corrosion, for example, of vacuum apparatus to be used, and of pollution, for example, of a gas discharge space.

Anyway, the presence of oxygen interferes with the determination of fluorine by means of chlorine.

One of the objects of the invention is to provide a continuous determination method of fluorine with which the disadvantages are avoided at least to a considerable extent.

The invention is inter alia based on the recognition of the fact that this is possible by using a substance in a liquid or solid state which is to be reacted with the fluorine atoms and which does not attack the medium in question.

Therefore, the method mentioned in the preamble is characterized according to the invention in that elementary silicon is chosen as a material and is provided so as to be optically separated from the gas discharge space.

With the method according to the invention a method is indicated to continuously determine the concentration of fluorine atoms in a gas flow.

It has been found that the intensity of the radiation emitted during the reaction between silicon and fluorine atoms is proportional to the square of the concentration of fluorine atoms. As a result of this the method is very sensitive for the determination of small differences in the concentration of fluorine atoms.

Fluorine atoms are formed in the gas discharge space, for example, by photolysis or pyrolysis.

In the intensity determination it is of importance that the silicon is provided so as to be separated optically from the space, because in the formation of fluorine atoms radiation is often generated which impedes a good intensity determination.

The fluorine atoms are preferably formed in a gas discharge.

The method according to the invention is particularly suitable when in or after the gas discharge space an etching reaction with fluorine-containing compounds is carried out, in particular when in the etching reaction in or after the gas discharge space a layer present on a silicon substrate is etched, or in the etching reaction in or after the gas discharge space elemental silicon is etched.

Etching reactions are to be understood to mean herein reactions in which solids are converted into gaseous substances. These solids may be of an inorganic origin but also of an organic origin (for example, photolacquers).

Fluorine atoms can be formed in the gas discharge space from a multiplicity of fluorine compounds, both inorganic compounds (for example $SF_6$) and organic compounds (for example $CF_4$).

The gas discharge space may be, for example, of the so-called barrel type, in which electrodes or a coil for obtaining a high-frequency field are present outside the space, or of the so-called pancake type, in which electrodes are present in the space.

Optical separation between the gas discharge space and the place where the intensity of the luminescent radiation is measured, can be obtained in a comparatively simple manner, due to the long life of the fluorine atoms, by providing the elemental silicon, the radiation of which is measured in a pump line, beyond the gas discharge space.

By means of the method according to the invention at least approx. $10^{14}$ atoms per $cm^3$, i.e. approx. 1 part per million, can be demonstrated in air at room temperature. As a gas chromatographic detector, the limit lies at approx. 0.1 ng per second. These minimum limits are a function of the temperature and decrease when the temperature increases.

The invention will now be described in greater detail with reference to an example and the accompanying drawing.

Figure 2:
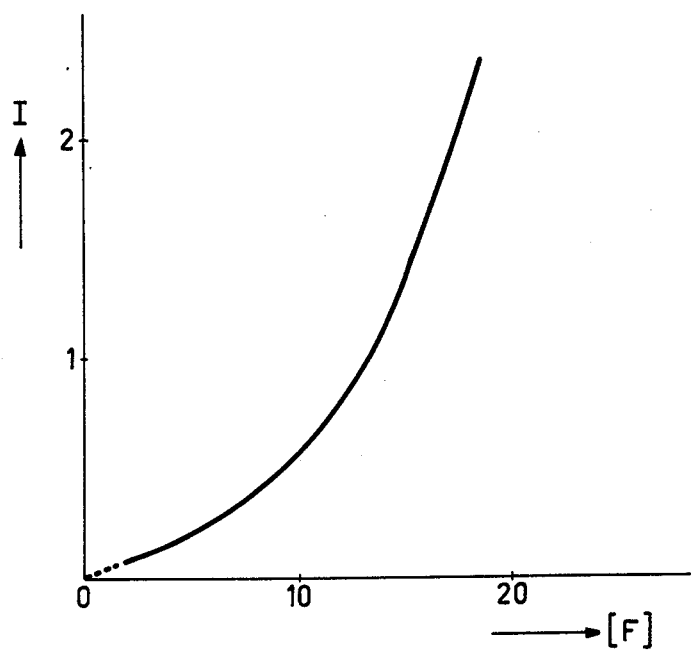

FIG. 1 of the drawing is a diagrammatic cross-sectional view of a part of a device for carrying out the method according to the invention and FIG. 2 shows diagrammatically the relationship between intensity and concentration as measured by means of an embodiment of the method in accordance with the invention.

In the example of the method of determining the concentration of fluorine in a gas flow, the gas flow 1 is passed through a space 2 in which a gas discharge in a high-frequency field is created in the usual manner by means of turns 3.

In the gas discharge, fluorine atoms are formed from compounds in the gas flow, which atoms, after leaving the gas flow of the gas discharge space 2, are reacted with a substance 4 while emitting luminescent radiation, the intensity of the radiation being measured.

According to the invention elemental silicon is chosen as a substance 4 and this substance is provided so as to be separated optically from the gas discharge space 2.

The radiation 5 has a wavelength of approx. 400–800 nm and is detected through the window 9 by means of, for example, a photo-multiplier 6.

The elemental silicon is provided in a pump line 7 of the gas discharge space or in a branch 8 of the pump line 7, so that optical separation can be obtained in a simple manner.

The elemental silicon 4 is provided, for example, in the form of a disk.

A measured relationship between intensity in $\mu A$ and concentration $\times 10^{14}$ cm$^3$ is shown in FIG. 2. From this it appears that the method is very sensitive to the measurement of concentration differences.

An etching reaction with fluorine-containing compounds can be carried out in the gas discharge space 1. When measuring the concentration in the gas flow 1 which leaves the space 2 the etching variation can be followed.

This applies, for example, when a layer, for example, of silicon dioxide on a silicon substrate or/and the silicon substrate itself have to be etched.

Of course the method according to the invention is not restricted to the example described. It will be obvious to those skilled in the art that there are many other fields of technology where the method according to the invention of determining fluorine can be used.

What is claimed is:

1. A method of continuously determining concentration of varying amounts of fluorine in a gas flow comprising the steps of
   passing said gas flow through a gas discharge space to form a varying number of fluorine atoms,
   separating a disk of elemental silicon from visible exposure to said gas discharge space by placing said disk in a branch line of a flow-through chamber downstream from said gas discharge space,
   reacting said fluorine atoms with said disk of elemental silicon in said branch line of said flow-through chamber,
   emitting luminescent radiation from said disk by said reaction with said fluorine atoms, and
   measuring intensity of said radiation to continuously determine the fluorine concentration.

2. A method according to claim 1, wherein said luminescent radiation is detected through a window in said branch line.

* * * * *

UNITED STATES PATENT AND TRADEMARK OFFICE
CERTIFICATE OF CORRECTION

PATENT NO. : 4,666,857
DATED : May 19. 1987
INVENTOR(S) : Cornelis I.M. Beenakker et al It is certified that error appears in the above-identified patent and that said Letters Patent is hereby corrected as shown below:

Column 4. after line 20 insert:

--3. A method according to claim 1, wherein said elemental silicon is maintained at an elevated temperature.--

On the title page "2 Claims" should read -- 3 Claims --.

Signed and Sealed this

Thirteenth Day of September, 1988

*Attest:*

DONALD J. QUIGG

*Attesting Officer*  *Commissioner of Patents and Trademarks*